US008668928B2

(12) United States Patent
Rand

(10) Patent No.: US 8,668,928 B2
(45) Date of Patent: Mar. 11, 2014

(54) CAPSULE

(75) Inventor: Paul Kenneth Rand, Ware (GB)

(73) Assignee: Glaxo Group Limited, Brentford, Middlesex (GB)

(*) Notice: Subject to any disclaimer, the term of this patent is extended or adjusted under 35 U.S.C. 154(b) by 918 days.

(21) Appl. No.: 12/732,519

(22) Filed: Mar. 26, 2010

(65) Prior Publication Data

US 2010/0175698 A1 Jul. 15, 2010

Related U.S. Application Data

(62) Division of application No. 10/535,453, filed as application No. PCT/EP03/13074 on Nov. 18, 2003, now Pat. No. 7,713,518.

(30) Foreign Application Priority Data

Nov. 20, 2002 (GB) .................................. 0227128.6

(51) Int. Cl.
  *A61K 9/48* (2006.01)
  *B65B 1/16* (2006.01)
  *A61M 15/00* (2006.01)
  *B65D 83/06* (2006.01)
(52) U.S. Cl.
  USPC ......................... 424/453; 141/67; 128/203.15
(58) Field of Classification Search
  USPC ............ 128/200.11–200.13, 200.14–200.24, 128/203.12–203.15, 203.23, 203.24; 141/18, 21–29, 67; 424/46, 451; 206/530, 539, 828; 433/90
  See application file for complete search history.

(56) References Cited

U.S. PATENT DOCUMENTS

| 330,970 A | * | 11/1885 | Ellis ......................... 128/204.13 |
| 1,410,556 A | * | 3/1922 | Dorment .................. 128/203.24 |
| 2,103,520 A | | 12/1937 | Donnelly |
| 2,587,215 A | | 2/1952 | Priestly |
| 2,590,832 A | | 3/1952 | Brown |
| 2,642,063 A | | 6/1953 | Brown |
| 4,095,587 A | | 6/1978 | Ishikawa |
| 4,265,236 A | * | 5/1981 | Pacella ..................... 128/203.23 |
| 4,391,590 A | | 7/1983 | Dougherty |
| 4,446,862 A | | 5/1984 | Baum et al. |

(Continued)

FOREIGN PATENT DOCUMENTS

| DE | 837157 | 4/1952 |
| EP | 0406893 | 1/1991 |

(Continued)

OTHER PUBLICATIONS

EP Search Report dated Jul. 23, 2008.

*Primary Examiner* — Justine Yu
*Assistant Examiner* — Valerie L Skorupa
(74) *Attorney, Agent, or Firm* — James P. Riek

(57) ABSTRACT

A capsule for a powder has a body which is provided with an internal chamber to hold the powder and first and second openings to an exterior environment. The body is adapted to be displaced from a filling state, in which the first and second openings are placed in fluid communication with one another through the internal chamber thereby enabling an airflow to be created through the body from the second opening to the first opening which is able to entrain powder in the exterior environment into the internal chamber for filling thereof, to a sealing state in which the internal chamber is sealed from the exterior environment so as to retain the powder held therein.

35 Claims, 3 Drawing Sheets

(56) References Cited

U.S. PATENT DOCUMENTS

| | | | |
|---|---|---|---|
| 4,767,326 | A | 8/1988 | Bennett et al. |
| 4,815,625 | A | 3/1989 | Filhol et al. |
| 5,048,514 | A | 9/1991 | Ramella |
| 5,152,284 | A * | 10/1992 | Valentini et al. ......... 128/203.21 |
| 5,287,850 | A | 2/1994 | Haber et al. |
| 5,310,082 | A | 5/1994 | Coustenoble |
| 5,372,128 | A | 12/1994 | Haber et al. |
| 5,379,763 | A | 1/1995 | Martin |
| 5,562,918 | A | 10/1996 | Stimpson |
| 5,595,175 | A | 1/1997 | Malcher et al. |
| 5,617,971 | A | 4/1997 | Eason et al. |
| 5,673,686 | A | 10/1997 | Villax et al. |
| 5,727,546 | A | 3/1998 | Clarke et al. |
| 5,769,070 | A | 6/1998 | Frati et al. |
| 5,778,873 | A * | 7/1998 | Braithwaite ............. 128/203.15 |
| 5,797,392 | A | 8/1998 | Keldmann et al. |
| 5,881,721 | A | 3/1999 | Bunce et al. |
| 5,896,855 | A | 4/1999 | Hobbs et al. |
| 5,924,417 | A | 7/1999 | Braithwaite |
| 6,098,619 | A * | 8/2000 | Britto et al. ............. 128/203.15 |
| 6,102,036 | A | 8/2000 | Zamel et al. |
| 6,109,261 | A | 8/2000 | Clarke et al. |
| 6,357,490 | B1 | 3/2002 | Johnston et al. |
| 6,371,111 | B1 * | 4/2002 | Ohki et al. ............. 128/203.15 |
| 6,470,884 | B2 | 10/2002 | Hörlin |
| 6,503,084 | B2 | 1/2003 | Evers et al. |
| 6,595,210 | B2 * | 7/2003 | Ohki et al. ............... 128/203.15 |
| 6,684,917 | B2 * | 2/2004 | Zhu et al. ......................... 141/18 |
| 6,708,884 | B1 | 3/2004 | Su et al. |

FOREIGN PATENT DOCUMENTS

| | | |
|---|---|---|
| EP | 0928618 | 7/1999 |
| EP | 1245243 | 10/2002 |
| GB | 367560 | 2/1932 |
| GB | 367580 | 2/1932 |
| GB | 959383 | 6/1964 |
| GB | 2323942 | 10/1998 |
| GB | 2340758 | 3/2000 |
| JP | 62122901 | 6/1987 |
| WO | 89/02289 | 3/1989 |
| WO | 95/31238 | 11/1995 |
| WO | 99/58180 | 11/1999 |
| WO | 00/01437 | 1/2000 |
| WO | 01/07107 | 2/2001 |
| WO | 01/17595 | 3/2001 |
| WO | 01/28617 | 4/2001 |
| WO | 01/30430 | 5/2001 |
| WO | 02/13897 | 2/2002 |
| WO | 02/096489 | 12/2002 |
| WO | 02/098495 | 12/2002 |
| WO | 03/030974 | 4/2003 |
| WO | 03/035151 | 5/2003 |
| WO | 03/047670 | 6/2003 |
| WO | 03/061743 | 7/2003 |
| WO | 2004/045688 | 6/2004 |

* cited by examiner

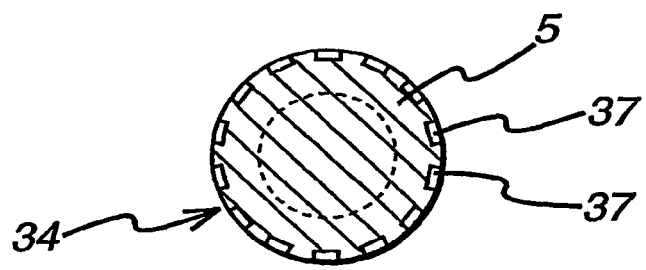
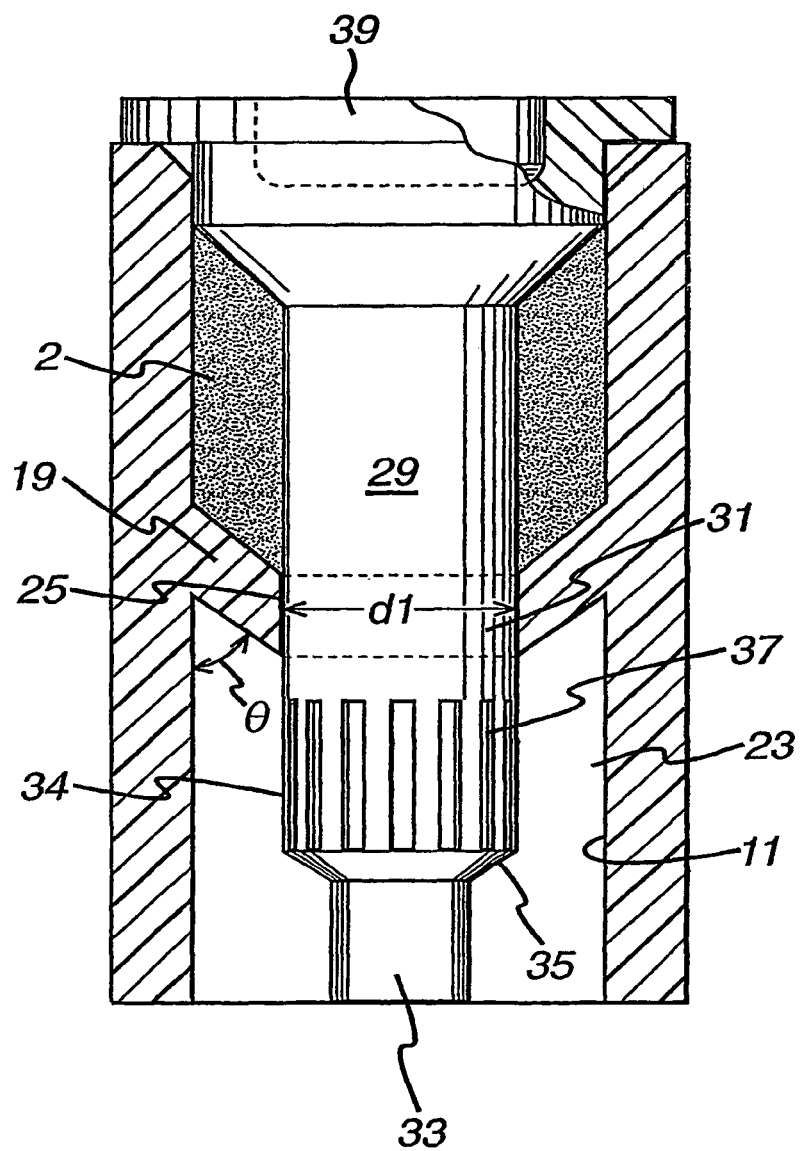

CAPSULE

CROSS-REFERENCE TO RELATED APPLICATIONS

This application is a divisional application of U.S. application Ser. No. 10/535,453, filed May 19, 2005, now allowed, a National Stage filing under 35 USC §371 of PCT/EP2003/013074 filed Nov. 18, 2003, which claims priority from GB Application No. 0227128.6 filed Nov. 20, 2002, the entire contents of all of the foregoing being specifically incorporated herein by reference.

FIELD OF THE INVENTION

The present invention relates to a capsule for holding a powder and is particularly, but not exclusively, concerned with such a capsule for containing a pharmaceutical powder, for instance an inhalable pharmaceutical powder.

BACKGROUND OF THE INVENTION

Dry powder inhalation devices ("DPI" for short) are well established for use in treating respiratory diseases. As an example, there may be mentioned the DISKUS® device of GlaxoSmithKline. In general, the pharmaceutical composition is formulated as a respirable powder and the powder is divided into a plurality of unit doses, each dose contained in its own sealed enclosure, for example blisters on a dosing strip. In use of the inhaler, the enclosures are opened, one at a time, by an opening mechanism of the inhalation device and the powder dose entrained into a patient's respiratory tract by an airflow generated through the device by the patient inhaling at a mouthpiece of the device.

Some of the sealed enclosures used in DPIs are difficult to fill with a unit dose of the pharmaceutical powder. It is an aim of the invention to provide a capsule for holding a powder which facilitates its filling with the powder.

As background art there may be mentioned WO01/07107, WO02/096489, U.S. Pat. No. 2,587,215, U.S. Pat. No. 4,446,862, and GB-A-2323042.

SUMMARY OF THE INVENTION

According to the present invention there is provided a capsule for a powder having a body which is provided with an internal chamber to hold the powder and first and second openings to an exterior environment, the body adapted to be displaced from a filling state, in which the first and second openings are placed in fluid communication with one another through the internal chamber thereby enabling creation of an airflow through the body from the second opening to the first opening which is able to entrain powder in the exterior environment into the internal chamber for filling thereof, to a sealing state in which the internal chamber is sealed from the exterior environment so as to retain the powder held therein.

The invention also provides a method of providing a capsule filled with a powder having the steps of providing a capsule according to the invention in its filling state, creating an airflow through the body of the capsule in a direction from the second opening to the first opening to cause powder from a powder source disposed externally of the capsule to be entrained into the internal chamber of the body, and moving the capsule to its sealing state.

The airflow through the capsule body may be created by applying a vacuum at the first opening of the capsule body.

Preferred features of the invention are set forth in the subordinate claims appended hereto, as well as in the non-limiting exemplary embodiment of the invention hereinafter described with reference to the accompanying FIGURES of drawings.

BRIEF DESCRIPTION OF THE DRAWINGS

FIG. 2 is a cross-sectional view of the piston part along line II-II in FIG. 1 showing a circumferential array of longitudinal channels formed in a portion of the outer surface of the piston part.

FIG. 3 is a part sectional side view of the capsule showing the piston part in a sealed position in the sleeve part with the powder product contained in a sealed chamber defined between the piston and sleeve parts.

DETAILED DESCRIPTION OF THE EXEMPLARY EMBODIMENT OF THE INVENTION

Figure 1:
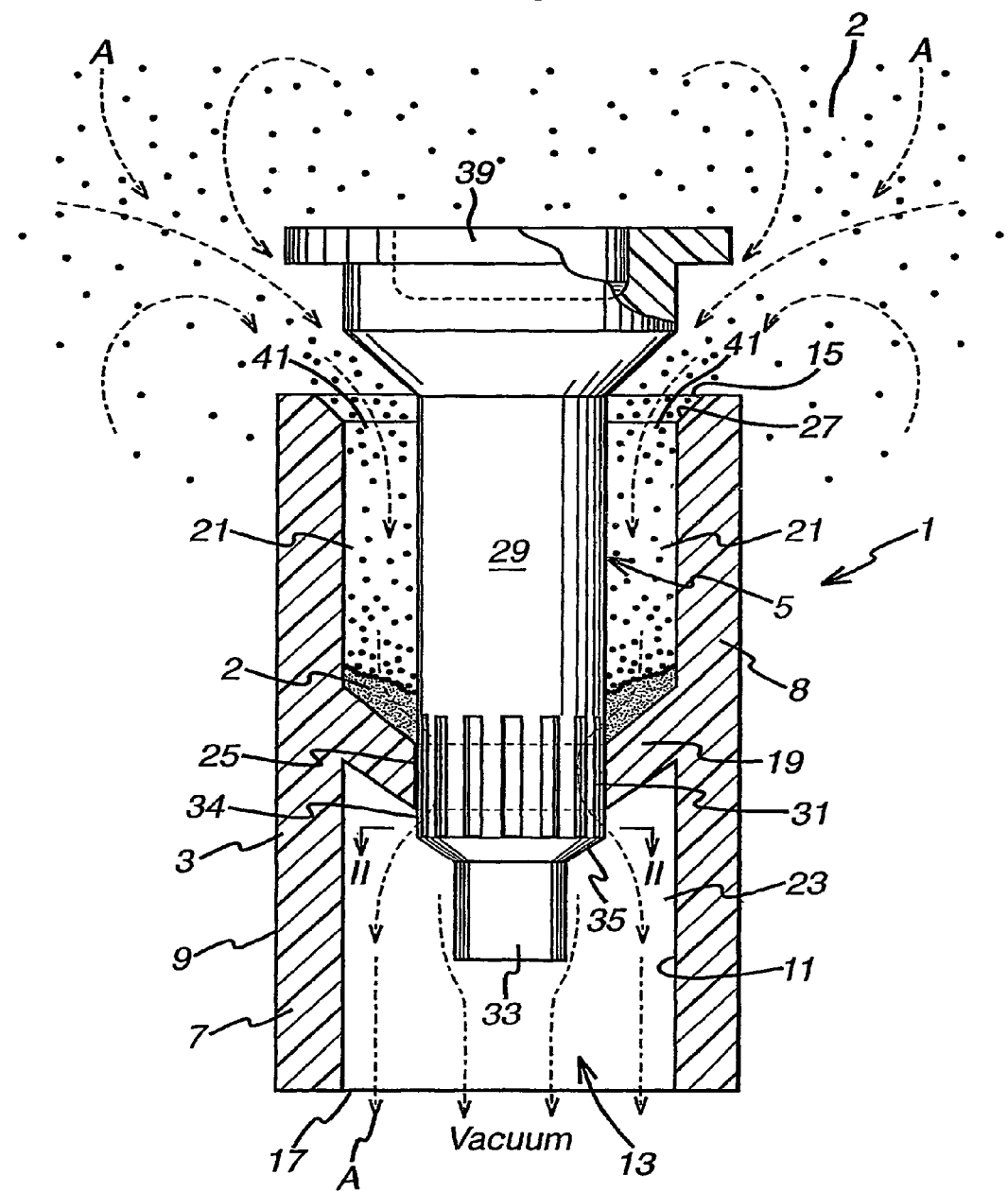
FIG. 1 is a part sectional side view of a capsule for a powder product in accordance with the present invention in a filling position, the capsule comprising a sleeve part and a piston part slidably mountable in the sleeve part.

In the FIGURES of drawings there is shown a generally cylindrical capsule 1 adapted to be filled with a powder product 2. The capsule 1 has particular application for dry powder products, more particularly dry powder pharmaceutical formulations for inhalation by a patient. The capsule 1 may be used in a dry powder inhaler.

The capsule 1 has a two-part construction comprising a generally cylindrical outer sleeve part 3 and a generally cylindrical inner piston part 5. The capsule 1 is preferably made from air- and moisture-proof materials, especially if the powder 2 is hygroscopic, as is the case with many pharmaceutical powders. Where the capsule is for a pharmaceutical powder, the material is an inert pharmaceutically acceptable material.

The outer sleeve part 3 has an annular wall 8 having an outer circumferential surface 9 and an inner circumferential surface 11. The inner circumferential surface 11 bounds an axial bore 13 which passes through the sleeve part 3 from an upper open end 15 to a lower open end 17. The upper open end 15 has a countersunk entrance 27.

The inner circumferential surface 11 is shaped to define a restriction 19 in the bore 13 to divide the bore 13 into an upper section 21 and a lower section 23. The restriction 19 in this embodiment takes the form of a step or shoulder which extends radially into the bore 13 to define an intermediate bore section 25 of narrower inner diameter than that of the upper and lower sections 21, 23. The restriction 19 in the bore 13 is resiliently deformable such that, on application of a downward force thereon, it is able to be deflected downwardly towards the lower open end 17 and, on release of the downward force, it returns to its undeformed position. This allows the piston part 5 to be held in place in the sleeve part 3 in different sliding positions, and for a dynamic seal to be formed between the sleeve and piston parts 3, 5.

The sleeve part 3 is preferably made from a plastics material, for instance by a moulding process, such as injection moulding or micro-moulding.

The sleeve part 3 may have a length (height) in the range of about 5 mm to about 15 mm and an outer diameter in the range of about 3 mm to about 8 mm. In other words, the capsule 1 may be referred to as a "microcapsule". The bore 13 may have an inner diameter (in the upper and lower sections 21, 23) in the range of about 1 mm to about 6 mm. Such a capsule 1 is suited for holding a unit dose of a pharmaceutical powder in the range of about 2 μg to about 30 mg. The capsule 1 may contain a unit dose of pure active drug substance, or a blend of pure active drug substances, in the range of about 2 μg to about 250 μg (i.e. no bulk filler), or a bulked out unit dose of a pharmaceutical powder up to about 30 mg.

For a small unit dose of pharmaceutical powder, for instance in the range of about 2-250 μg, it is preferable for the sleeve part 3 to have a length (height) in the range of about 5 mm to about 6 mm, an outer diameter in the range of about 3 mm to about 5 mm, and an inner diameter in the range of about 1 mm to about 3 mm, more preferably about 2 mm.

Turning now to the piston part 5, as shown in FIGS. 2 and 3 this has a shank 29 of a general cylindrical cross section. The shank 29 has an upper section 31, a lower section 33 of smaller outer diameter than the upper section 31, and a flared section 35 connecting the upper and lower sections 31, 33. A series of longitudinal grooves or flutes 37 is circumferentially arranged about a lower end portion 34 of the upper shank section 31.

Figure 4:
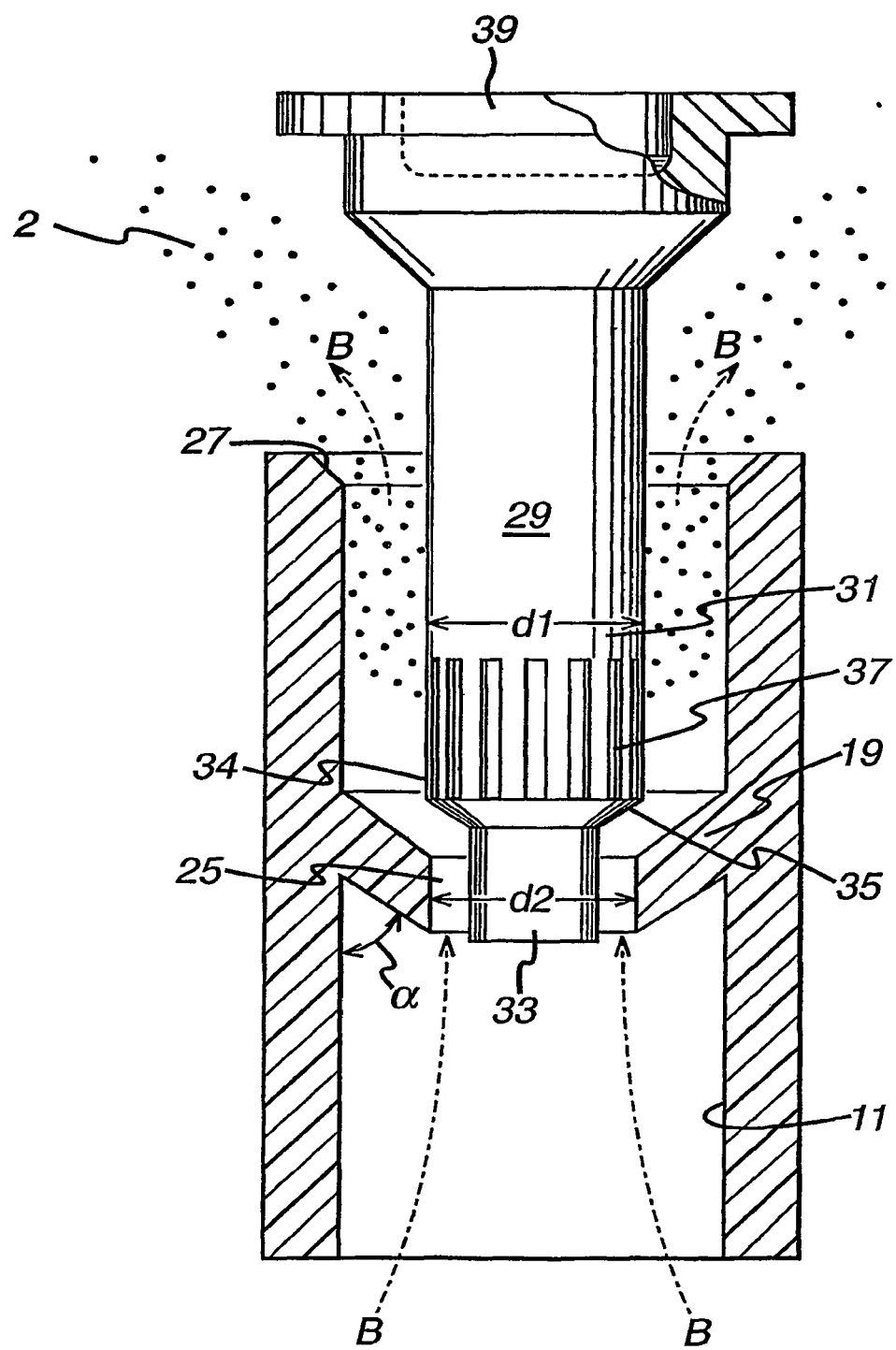
FIG. 4 is a part sectional side view of the capsule with the piston part in a discharge position relative to the sleeve part.

As shown most clearly in FIG. 4, the upper section 31 of the shank 29 has an outer diameter d1 which is the same, or, more typically, greater than the 'normal' inner diameter d2 of the intermediate section 25 of the bore 13 in the sleeve part 3. Thus, the upper section 31 of the shank 29 fits in the intermediate section 25 with an interference fit, the resiliently deformable nature of the restriction 19 facilitating the formation of the interference fit, especially when the outer diameter d1 of the upper section 31 of the shank 29 is greater than the inner diameter d2 of the intermediate section 25 of the bore 13. In this particular embodiment, the inner diameter d2 of the intermediate bore section 25 is less than the outer diameter d1 of the upper shank section 31, as will be appreciated by a comparison of FIGS. 3 and 4.

At an upper end of the shank 29 there is provided a co-axially arranged piston head 39 of larger outer diameter than the shank 29.

The piston part 5 is also preferably made from a plastics material, for instance by a moulding process, such as injection moulding or micro-moulding.

In use, the piston part 5 is first slidably mounted in the sleeve part 3 in a filling position shown in FIG. 1. In the filling position, the upper section 31 of the shank 29 of the piston part 5 is slidably received in the intermediate section 25 of the bore 13 so as to be held in frictional engagement therewith such that the longitudinal grooves 37 place the upper and lower bore sections 21, 23 in fluid communication with one another. In this regard, it will be noted that the longitudinal grooves 37 have a longer longitudinal dimension than that of the intermediate section 25 of the bore 13. Placing the piston part 5 in the filling position spaces the piston head 39 above the upper open end 15 of the bore 13, as further shown in FIG. 1. In this way, an inlet path 41 into the upper section 21 of the bore 13 is defined.

With the piston part 5 in its filling position, application of a vacuum to the lower open end 17 of the sleeve part 3 draws powder particles 2 from a particle cloud in the exterior environment around the capsule 1 into the upper bore section 21 through the inlet path 41 as a result of the vacuum pressure acting in the upper bore section 21 through the longitudinal grooves 37. This is shown diagrammatically in FIG. 1 by the arrows A.

The longitudinal grooves 37 are sized such that the powder particles 2 are occluded therein. This does not prevent the vacuum from creating the negative pressure in the upper bore section 21 in the filling position, but prevents the powder 2 from seeping from the upper bore section 21 to the lower bore section 23. As an example, the grooves 37 may have a depth in the range of substantially 0.005-0.01 mm, preferably substantially 0.007 mm.

Once the upper bore section 21 has been filled with the required dose of powder 2, for example a unit dose of a pharmaceutical powder, the vacuum is removed and the piston part 5 slid downwardly in the sleeve part 3 to a sealed position shown in FIG. 3. The sliding movement of the piston part 5 to the sealed position results in:

(i) The longitudinal grooves 37 moving out of the intermediate bore section 25 into the lower bore section 23 to bring the upper shank section 31 into sealing, frictional engagement with the intermediate section 25.

(ii) The piston head 39 being brought into sealing engagement with the countersunk entrance 27 of the bore 13.

This prevents or inhibits ingress of air or moisture into the upper bore section 21 and prevents egress of the powder 2 from the capsule 1. So, in the sealed position the powder 2 drawn into the upper bore section 21 is sealably contained therein.

When the dose of powder 2 in the upper bore section 21 is required to be discharged, the piston part 5 is slid upwardly to a discharge position shown in FIG. 4. In the discharge position of the piston part 5, the piston head 39 is spaced upwardly of the upper open end 15 of the sleeve part 3 and the lower section 33 of the shank 29 is positioned in the intermediate bore section 25. In this way, an airflow path indicated by the arrows B is provided which enables the powder 2 in the upper bore section 21 to be discharged from the capsule 1 out of the upper open end 15 of the sleeve part 3. The powder 2 may be discharged in this way by application of a positive air pressure to the bore 13 of the sleeve part 3 through the lower open end 17.

The resilience of the restriction 19 will be appreciated by comparing the angle θ that the restriction 19 makes with the inner circumferential surface 11 in the sealed state shown in FIG. 3 with the 'return' or 'normal' angle α it makes in the discharging state shown in FIG. 4.

Appropriate medicaments for the inhalable pharmaceutical powder for use in the present invention may be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are an anti-inflammatory agent (for example a corticosteroid or an NSAID), an anticholinergic agent, a $\beta_2$-adrenoreceptor agonists, an antiinfective agent (e.g. an antibiotic or an antiviral) and an antihistamine. The medicament may be the sole medicament in the capsule or in combination with another medicament. Preferred combinations are based on the preferred medicament list above.

Preferred as a component of a medicament combination in the capsule are albuterol, salmeterol, fluticasone propionate and beclomethasone dipropionate and salts or solvates thereof, e.g., the sulphate of albuterol and the xinafoate of salmeterol.

A particularly preferred medicament combination for use in the capsule of the invention is a bronchodilator in combination with an anti-inflammatory. The bronchodilator is suitably a beta-agonist, particularly a long-acting beta-agonist (LABA). Suitable bronchodilators include salbutamol (e.g., as the free base or the sulphate salt), salmeterol (e.g., as the xinafoate salt) and formoterol (e.g., as the fumarate salt). The anti-inflammatory is suitably an anti-inflammatory steroid. Suitable anti-inflammatory compounds include a beclomethasone ester (e.g., the dipropionate), a fluticasone ester (e.g., the propionate) or budesonide or any salt or solvate thereof. One preferred combination is fluticasone propionate and salmeterol, or any salt or solvate thereof (particularly the xinafoate salt). A further preferred combination is budesonide and formoterol or any salt or solvate thereof (e.g. formoterol as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as a pure drug or together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient. The excipient may be included with the medicament via well-known methods, such as by admixing, co-precipitating and the like.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

It will be understood that the embodiment described hereinabove may be varied and modified in many different ways and adopt other guises within the scope of the appended claims. With this in mind, the use of reference numerals in the appended claims is for illustration only, and not meant to have a limiting effect on the scope of the claims. Finally, the use of prefixes such as "substantially" and "generally" etc. to numeric values, geometries and other parameters in the specification is meant to include the exact numeric value, geometry and parameter.

What is claimed is:

1. A capsule for a powder, said capsule having a body which is provided with an internal chamber to hold the powder and first and second openings to an exterior environment, said second opening and said internal chamber having a common major dimension, the body adapted to be displaced from a filling state, in which the first and second openings are placed in fluid communication with one another through the internal chamber thereby enabling creation of an airflow through the body from the second opening to the first opening which is able to entrain powder in the exterior environment into the internal chamber for filling thereof with the powder, to a sealing state in which the internal chamber is sealed from the exterior environment so as to retain the powder held therein, in which the body has first and second parts which are moved relative to one another to bring the body to its filling and sealing states, wherein in the sealing state the first part is disposed in a first position relative to the second part in which it sealingly closes the first and second openings, and wherein in the filling state the first part is disposed in a second position relative to the second part in which it opens the first and second openings.

2. The capsule of claim 1 in which the filling and sealing states are, respectively, expanded and contracted states of the body.

3. The capsule of claim 1 wherein in the filling state of the body the first opening is partially obstructed to an extent which permits airflow therethrough, but which becomes occluded with powder entrained in the airflow.

4. The capsule of claim 1 in which the body is assembled in both the filling and sealing states.

5. The capsule of claim 4 wherein in the filling and sealing states the first part is mounted to the second part.

6. The capsule of claim 1, wherein in the filling state of the body, the first opening is partially obstructed to an extent which permits airflow therethrough, but which becomes occluded with powder entrained in the airflow, and in which the first part partially obstructs the first opening in the filling state.

7. The capsule of claim 6 in which the first part is partially plugged in the first opening in the filling state.

8. The capsule of claim 7 in which the first part has a plug section which is located in the first opening in the filling state, the plug section having an outer surface which, in the filling state, is at least in part spaced from an inner surface of the first opening.

9. The capsule of claim 8 in which the outer surface has first and second outer surface portions, wherein in the filling state the first outer surface portion is spaced from the inner surface of the first opening and the second outer surface portion abuts the inner surface of the first opening.

10. The capsule of claim 9 in which the first outer surface portion corresponds to one or more channels in the outer surface of the plug section.

11. The capsule of claim 8 in which the plug section is a first plug section and the first part has a second plug section which sealingly plugs the first opening in the sealing state.

12. The capsule of claim 11 in which the body is moved from the filling state to the sealing state by movement of the first part in a first direction relative to the second part, the first plug section being disposed, in use, on the first part in the first direction relative to the second plug section.

13. The capsule of claim 11 in which the first and second plug sections are contiguously arranged.

14. The capsule of claim 1 in which the first part sealingly plugs the second opening in the sealing state.

15. The capsule of claim 1 in which the first opening is formed in the second part.

16. The capsule of claim 15 in which the second part is a sleeve part with an internal passageway which connects the first and second openings.

17. The capsule of claim 16 in which the first opening is formed by a restriction in the passageway.

18. The capsule of claim 17 in which the restriction is formed by an inwardly directed shoulder in the passageway.

19. The capsule of claim 16 in which the second opening is formed at an end of the internal passageway.

20. The capsule of claim 16 in which the first part is slidably mounted in the passageway and the internal chamber is defined between the inner surface of the passageway and the outer surface of the first part.

21. The capsule of claim 1 in which the second opening is formed in the second part.

22. The capsule of claim 1 in which the first part is mounted in the second part for sliding movement relative thereto.

23. The capsule of claim 1 in which the internal chamber is defined between the first and second parts.

24. The capsule of claim 1 wherein in the filling state the first part extends through the second opening to leave a gap therebetween for ingress of the entrained powder into the internal chamber and wherein in the sealing state the first part is moved into sealing relation in the second opening.

25. The capsule of claim 24 in which the first part has a cap section which, in the filling state, is spaced exteriorly of the second opening, but which in the sealing state is sealingly seated in the second opening.

26. The capsule of claim 25 in which the first part has a plug section which is located in the first opening in the filling state, the plug section having an outer surface which, in the filling state, is at least in part spaced from an inner surface of the first opening, and in which the first part has a shank section connecting the cap section to the plug section.

27. The capsule of claim 1 in which the first and second parts are further movable relative to one another to bring the body from the sealing state to a discharging state in which an airflow is able to be produced through the body from the first opening to the second opening to entrain the powder in the internal chamber into the exterior environment.

28. The capsule of claim 27 in which the first part has a plug section which is located in the first opening in the filling state, the plug section having an outer surface which, in the filling state, is at least in part spaced from an inner surface of the first opening, wherein the first part has a section with a transverse dimension which is less than the corresponding dimension of the plug section, the section being located with respect to the plug section such that in the discharging state it is brought into registration with the first opening.

29. The capsule of claim 1 comprising a pharmaceutical powder in the internal chamber.

30. The capsule of claim 29 having a unit dose of the pharmaceutical powder in the internal chamber.

31. An inhalation device comprising one or more capsules according to claim 30.

32. The capsule of claim 1 in which the internal chamber is the sole internal chamber.

33. The capsule of claim 1 in which the first opening is partially obstructed by a series of longitudinal grooves or flutes sized such that powder particles are occluded therein.

34. The capsule of claim 33 in which the longitudinal grooves or flutes have a depth in the range of substantially 0.005 mm to 0.01 mm.

35. The capsule of claim 34 in which the longitudinal grooves or flutes have a depth of substantially 0.07 mm.

* * * * *